May 16, 1972 H. W. MOTZKAU Plant Pat. 3,172
AZALEA PLANT
Filed July 20, 1970
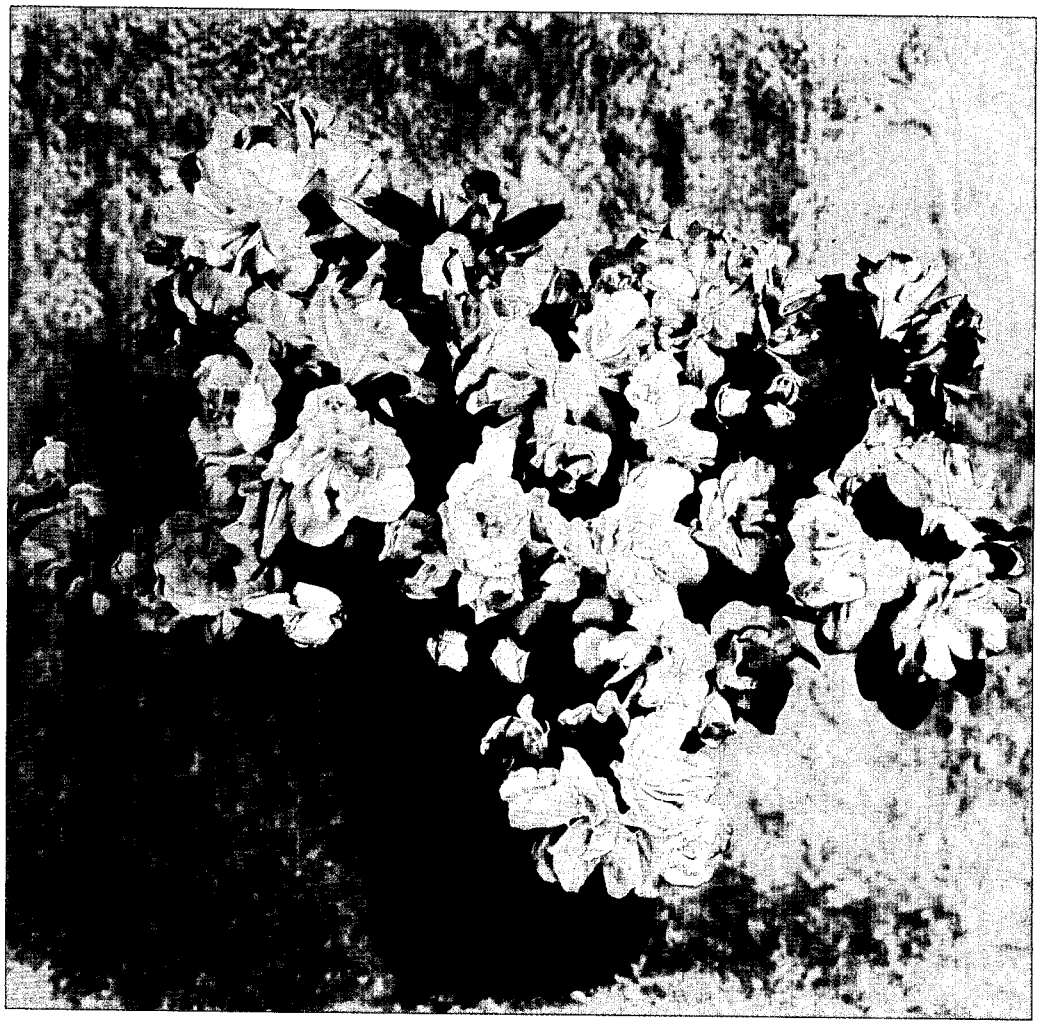
INVENTOR
HENRY W. MOTZKAU
BY
Oberlin, Maky, Donnelly & Renner
ATTORNEYS United States Patent Office Plant Pat. 3,172
Patented May 16, 1972

3,172
AZALEA PLANT

Henry W. Motzkau, Whitewater, Wis., assignor to Yoder Brothers, Inc., Barberton, Ohio Filed July 20, 1970, Ser. No. 56,760
Int. Cl. A01h 5/00
U.S. Cl. Plt.—56 1 Claim The present invention comprises a new and distinct variety of azalea plant which has resulted from crossing certain azalea selections in a program of hybridization. The seed parent is unnamed and unpatented, and identified for breeding purposes as seedling #331. The pollen parent is the unpatented variety, Cascade.

The new variety is similar in certain respects to Skylark, an unpatented but well-known commercial variety, having the same characteristics as Skylark of rapid growth, keeping quality and irregular shoot differentiation. The new variety is distinguished from Skylark by the following characteristics:

(1) The new variety is lavender pink in color compared to the medium pink color of Skylark.

(2) The new variety has lighter green foliage with smaller, less pointed leaves than Skylark.

(3) The new variety responds as an early season in contrast to the mid-season response of Skylark.

(4) The new variety buds easier and more uniformly in both year around and natural programs than Skylark.

(5) The new variety forces more uniformly and in less time than Skylark.

(6) The new variety can be put in the cooler with less mature buds than Skylark and will develop and flower uniformly.

(7) The new variety has added durability in the home. It will keep at least one week longer and shows fewer tendencies for petal margin dehydration than Skylark.

The new variety was selected from progeny of seedlings from the above mentioned parents. Varietal worth was determined by flowering liners built up from the initial selection in both year round and natural season developmental flowering programs over a period of 5 years. Stock growth was evaluated in the vicinity of Fort Myers, Fla.

My new variety has been asexually reproduced by cuttings at Whitewater, Wis., and has been found to retain its distinctive characteristics through successive propagations.

My new variety when grown in the vicinity of Barberton, Ohio has a response described as early season, although it will be understood that the response time and blooming period may vary significantly with varying environmental conditions such as temperature and amount of daylight. Suggested flowering period is from mid-December through March in a natural season program in all areas of the United States, and is year-round (all 12 months) in a controlled flowering program for everywhere in the United States.

The accompanying drawing shows the unique features of my new variety, the colors being as nearly true as possible with color illustrations of this type.

The following is a detailed description, including color designations of my new variety, based on observations made of the new variety in a greenhouse in Barberton, Ohio. The color references are to the Munsell Color Book, 1963 edition:

Botanical classification: *Rhododendron hybrida,* evergreen type.

Flower:

*Color.*—Lavender pink (Spring color at Barberton, Ohio)—general tonality—lavender pink 3.75RP5/12—sepals first divide—light lavender pink 5RP6/6—petals unfurl—lavender pink near 3.75RP5/12—inside petals—lavender pink 3.75-RP5/12—reverse petals—lavender pink 3.75RP-5/12 but lighter—base of petals—light pink near 5RP7/6, mostly translucent—discoloration—retains color for 3 weeks followed by gradual fading and oxidation.

*Bud.*—Size—medium — form — pointed — opening habit—open, cup-like, retains cup-like form.

*Bloom.*—Size—medium; average—2¼"; range—2"–2¾"—borne—several together; average, 3; range, 1–5—form—double. All stamens petaloid to varying degrees.

*Blooming habit.*—Once, profusely. Early season—response—natural season, mid-December–March year round—all 12 months—sepals—smooth, hairy, persistent—peduncle—length—long; aspect—hairy; strength—strong.

*Petals.*—Texture—soft — appearance — smooth; inside—satiny; outside — satiny — form — rounded, notched—arrangement—imbricate with petaloids—fragrance—none—persistence—long, shatter resistant—longevity—under green house conditions 3–4 weeks; under home conditions, 4–5 weeks.

*Reproductive organs.*—Stamen anthers—few, if any, mostly petaloid lavender pink 5RP5/10—filaments—none petaloid—style—columnar long, pink between 10RP6/10–5/10—stigmas—normal, surface tan near 5Yr5/6—ovaries—hypogynous.

Plant: Bush form.

*Growth habit.*—Compact, spreading growth regulators not need for compact growth and budding.

*Breaking habit.*—Vigorous, may be somewhat irregular.

*Size of average finished product grown from the standard #7 liner of Yoder Brothers, Inc., Barberton, Ohio.*—Height — 10"–12" — diameter—10"–15".

*Budding ease.*—Quite easy under a wide range of environmental conditions.

*Uniformity of budding.*—Excellent.

*Foliage.*—Type—evergreen—leaflets—single—size—quite variable; length—1¾"; average range—1¼"–2½", width—⅞"; average range—½"–1¼"—shape—ovate to obovate—texture—upper, glossy; lower, glossy—rib and veins—slightly depressed—edge—smooth—color—new foliage upper—green between 5GY4/6 and 5GY5/6—lower—lit. green, draker than 5GY6/6 but not 5GY5/6—mature foliage upper—dark green 7.5GY3/4—lower—lt. green 7.5GY5/4—petiole—short, green 5GY6/6.

*Stems.*—Color of new wood—light green between 7.5GY6/6–5/6—color of mature wood—light brown between 10YR5/4–5/6.

*Recommended flowering period.*— Year round—all 12 months in controlled program—natural season—December–March. Can be flowered for Christmas anywhere in United States.

*Responsiveness to day length and temperature.*—Buds easily and uniformily under wide range of environmental conditions.

*Cooler tolerance.*—Excellent.

*Shipping tolerance.*—Excellent.

I claim:

1. A new and distinct variety of azalea characterized particularly as to novelty by its evergreen type foliage, its rapid growth, its ease of budding under variable conditions, its lavender pink color, its long-lastingness, its early profuse flowering, and its adaptability to year round flowering programs.

No references cited.

ROBERT E. BAGWILL, Primary Examiner